US007569359B2

(12) United States Patent
McDonnell et al.

(10) Patent No.: US 7,569,359 B2
(45) Date of Patent: Aug. 4, 2009

(54) INDICATOR DEVICE HAVING AN ACTIVE AGENT ENCAPSULATED IN AN ELECTROSPUN NANOFIBER

(75) Inventors: Gerald E. McDonnell, Basingstoke (GB); Anthony Fiorello, Willowick, OH (US); Daniel Smith, Stow, OH (US)

(73) Assignee: American Sterilizer Company, Mentor, OH (US)

( * ) Notice: Subject to any disclaimer, the term of this patent is extended or adjusted under 35 U.S.C. 154(b) by 829 days.

(21) Appl. No.: 10/965,350

(22) Filed: Oct. 14, 2004

(65) Prior Publication Data

US 2006/0083657 A1 Apr. 20, 2006

(51) Int. Cl.
*C12Q 1/22* (2006.01)
*C12M 1/34* (2006.01)
*G01N 31/22* (2006.01)
*G01N 21/77* (2006.01)

(52) U.S. Cl. .................. 435/31; 435/287.4; 435/287.8; 435/287.9; 435/805; 422/56; 422/57; 436/170

(58) Field of Classification Search .............. 435/287.4, 435/287.7–287.9, 34, 805
See application file for complete search history.

(56) References Cited

U.S. PATENT DOCUMENTS

| | | | | |
|---|---|---|---|---|
| 3,959,560 | A | 5/1976 | Sturwold et al. | 428/394 |
| 4,311,793 | A * | 1/1982 | Halleck | 435/31 |
| 4,430,277 | A | 2/1984 | Lin | 264/22 |
| 5,486,459 | A | 1/1996 | Burnham et al. | 435/31 |
| 5,487,889 | A | 1/1996 | Eckert et al. | 424/93.1 |
| 5,552,320 | A | 9/1996 | Smith | 435/287.4 |
| 5,834,384 | A | 11/1998 | Cohen et al. | 442/382 |
| 6,187,555 | B1 | 2/2001 | Tautvydas | 435/29 |
| 6,294,185 | B1 | 9/2001 | Worley et al. | 424/405 |
| 6,352,837 | B1 | 3/2002 | Witcher et al. | 435/31 |
| 6,566,090 | B2 | 5/2003 | Witcher et al. | 435/31 |
| 2003/0211618 | A1 | 11/2003 | Patel | 436/38 |
| 2003/0215624 | A1 | 11/2003 | Layman et al. | 428/221 |
| 2007/0113358 | A1 * | 5/2007 | Rabolt et al. | 8/500 |

FOREIGN PATENT DOCUMENTS

| | | |
|---|---|---|
| WO | WO 00/50634 | 8/2000 |
| WO | WO 01/10471 | 2/2001 |

OTHER PUBLICATIONS

Huang et al. 'A review on polymer nanofibers by electrospinning and their applications in nanocomposites.' Composites Science and Technology. vol. 63 (2003), pp. 2223-2253.*

Zhang, Wang, Feng, Li, Lim and Ramakrishna, "Coaxial Electrospinning of (Fluorescein Isothiocyanate-Conjugated Bovine Serum Albumin)-Encapsulated Poly(ε-caprolactone) Nanofibers for Sustained Release," Biomacromolecules, Apr. 2006 7(4), 1049-1057 (abstract included).

Kwoun et al., "A Novel Polymer Nanofiber Interface for Chemical and Biochemical Sensor Applications," Modeling and Simulation of Microsystems 2001, (www.cr.org), ISBN 0-9708275-0-4, pp. 338-341.

Jayesh Doshi and Darrell H. Reneker, "Electrospinning Process and Application of Electrospun Fibers," *Journal of Electrostatics* 35 (1995), pp. 151-160.

Jong-Sang Kim and Darrell H. Reneker, "Polybenzimidazole Nanofiber Produced by Electrospinning," The Institute of Polymer Science, The University of Akron, Akron, Ohio, *Polymer Engineering and Science*, May 1999, vol. 39, No. 5, pp. 849-854.

Darrell H. Reneker and Iksoo Chun, "Nanometre diameter fibers of polymer, produced by electrospinning," Maurice Morton Institute of Polymer Science, The University of Akron, Akron, Ohio, 1996, *Nanotechnology* 7, IOP Publishing Ltd., pp. 216-223.

Phillip Gibson, Heidi Schreuder-Gibson and Christopher Pentheny, "Electrospinning Technology: Direct Application of Tailorable Ultrathin Membranes," U.S. Army Soldier Biological & Chemical Command Soldier Systems Center, Natick, Massachusetts, *Journal of Coated Fabrics*, vol. 28, Jul. 1998, pp. 63-71.

Gokul Srinivasan and Darrell H. Renekert, "Structure and Morphology of Small Diameter Electrospun Aramid Fibers," Maurice Morton Institute of Polymer Secience, The University of Akron, Akron, Ohio, *Polymer International*, 1995, pp. 195-201.

Thomas B. Bruns, M.D. and J. Mack Worthington, M.D., "Using Tissue Adhesive for Wound Repair: A Practical Guide to Dermabond," University of Tennessee College of Medicine, Chattanooga, Tennesse, *American Family Physician*, Mar. 1, 2000, pp. 1-7.

Raimund Jaeger, Michel M. Bergshoef, Cristina Martin i Batlle, Holger Schönherr, G. Julius Vancuso, "Electrospinning of Ultra-Thin Polymer Fibers," Centre for Materials Research, University of Twente, Enschede, The Netherlands, *Macromolecular Symposia*, Feb. 1998, Hüthig & Wepf Verlag, Zug, Heidelberg, Oxford, Ct., pp. 140-151.

Sally Dabney, Woraphon Kataphinan, Darrell Reneker and Daniel Smith, "Direct Electrospun Nanofiber Wound Dressings," Department of Chemistry and Department of Polymer Science, University of Akron, Akron, Ohio, (Aug. 15, 2000).

Steven B. Warner, Proposal entitled: "Electrostatic Spinning and Properties of Ultrafine Fibers," University of Massachusetts, Dartmouth, Project No. M98-D01, (Oct. 19, 2000).

* cited by examiner

*Primary Examiner*—William H Beisner
(74) *Attorney, Agent, or Firm*—Kusner & Jaffe; Michael A. Centanni

(57) ABSTRACT

An indicator device for determining the efficacy of an antimicrobial treatment process. The indicator device includes an active agent encapsulated in an encapsulation component. The encapsulation components preferably takes the form of an electrospun nanofiber including a polymer.

27 Claims, 2 Drawing Sheets

INDICATOR DEVICE HAVING AN ACTIVE AGENT ENCAPSULATED IN AN ELECTROSPUN NANOFIBER

FIELD OF THE INVENTION

The present invention relates generally to an indicator device for determining the efficacy of an antimicrobial treatment process, and more particularly to an indicator device including an active agent encapsulated in an electrospun nanofiber.

BACKGROUND OF THE INVENTION

In the healthcare industry it is often necessary to determine the efficacy of an antimicrobial treatment process. As used herein, "antimicrobial treatment process" includes, but is not limited to, hand and machine washing, sterilization, disinfection, decontamination, inactivation, and sanitization processes. The effectiveness of such processes is typically verified by use of a biological indicator, a chemical indicator, or both. An indicator is typically comprised of (1) an active agent, such as a biological specimen (e.g., an enzyme from a biological source, a biological organism, or both) or a color changing chemical sensitive to a specific chemistry, and (2) a carrier substrate (i.e., support system) for supporting the active agent. Effectiveness of an antimicrobial treatment process may be indicated by a change in the color of the active agent. Alternatively, process effectiveness may be evaluated by exposing the active agent or its byproducts to a reagent (e.g., a growth media) that reacts therewith.

During an antimicrobial treatment process, the active agent may separate (e.g., wash off) from the carrier substrate due to exposure to the liquid or gaseous treatment chemicals used during the antimicrobial treatment process. Consequently, the indicator may operate improperly. In this regard, the indicator may have a lowered sensitivity, or have a total operation failure. Moreover, the separated active agent may also re-contaminate the item being treated.

The present invention provides an indicator device including an active agent embedded in an electrospun nanofiber to prevent the separation of the active agent from the carrier substrate.

SUMMARY OF THE INVENTION

In accordance with the present invention, there is provided an indicator device for use in determining the efficacy of an antimicrobial treatment process, comprising: (a) at least one active agent; (b) at least one encapsulation component for encapsulating the at least one active agent wherein said encapsulation component includes at least one of the following: a polymer; a polymer blend; and a mixture of a polymer and a plasticizer; and (c) a carrier substrate.

An advantage of the present invention is the provision of an indicator device that encapsulates an active agent in an electrospun nanofiber.

Another advantage of the present invention is the provision of an indicator device that prevents the separation of the active agent from a carrier substrate.

Still another advantage of the present invention is the provision of an indicator device that allows contact between the treatment chemistry of the antimicrobial treatment process and an active agent, without compromising the integrity of the active agent, the carrier substrate, or the articles being treated by the treatment chemistry.

Yet another advantage of the present invention is the provision of an indicator device suitable for process validation, indication, detection and the like, in connection with an antimicrobial treatment process.

Yet another advantage of the present invention is the provision of an indicator device suitable for neutralizing antimicrobial chemistry after a treatment process.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF A PREFERRED EMBODIMENT

Figure 1:
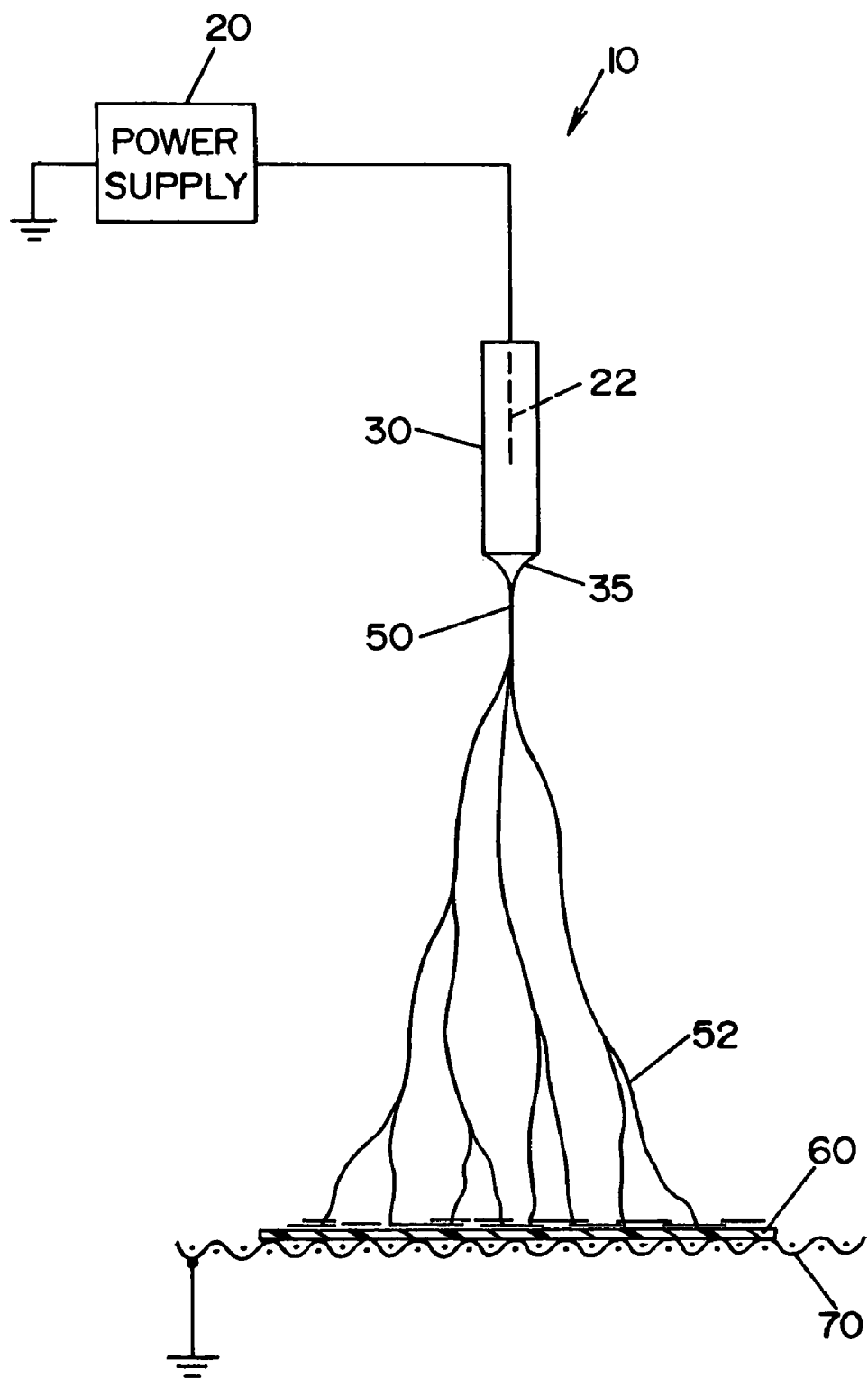
FIG. 1 is a schematic diagram of an apparatus for producing electrospun nanofibers.

Referring now to the drawings wherein the showings are for the purposes of illustrating a preferred embodiment of the invention only and not for purposes of limiting same, FIG. 1 shows a schematic diagram of an apparatus 10 for producing electrospun nanofibers. The electrospun nanofibers form a fabric or mat from an extrusion of plastic. The extrudate can incorporate at least one active agent. The fabric or mat formed by the extrudate thus provides a host for the active agent. Apparatus 10 is generally comprised of a high voltage power supply 20, an electrode 22, a capillary tube 30, and a collector electrode 70.

High voltage power supply 20 preferably produces a voltage in the range of 5 kV to 20 kV, and has a low current. Electrode 22 is connected to high voltage power supply 20 and extends into capillary tube 30. Capillary tube 30 is filled with a polymer solution 40. In a preferred embodiment, polymer solution 40 includes a polymer and a solvent used to solvate the polymer, as will be described in detail below. Alternatively, a polymer melt can be substituted for the polymer solution. Collector electrode 70 preferably takes the form of a metal plate, screen or grid. Collector electrode 70 is connected to ground.

Alternate arrangements of the electrodes can be made to allow for the generation of plasma in air or inert gases, or both, prior to, concurrent, or subsequent to the polymer discharge from capillary tube 30. Such electrode arrangements are known based upon the type and proximity of the electrodes, and the use of dielectric materials to minimize or eliminate arcing or filamentary discharge currents. Electrode configurations include dielectric barrier discharge such as resistive barrier discharge, hollow/microhollow cathode discharge, capillary plasma electrode and cathode boundary layer, and electromagnetic ion implantation such as microwave generated plasma, atmospheric plasma jet, and nitrogen gas ion implantation. In cases where plasma generation is incorporated into the electrospinning process, the applied voltages can be one to three orders of magnitude higher.

A carrier substrate 60 is preferably located proximate to collector electrode 70. In the illustrated embodiment carrier substrate 60 is located on top of collector electrode 70. Carrier substrate 60 supports the electrospun nanofibers formed thereon, as will be described in detail below. Carrier substrate 60 is preferably a rigid porous or nonporous material, as will be described in further detail below. In a preferred embodiment, carrier substrate 60 is selected for resistance to heat exposure, liquid chemicals, and gaseous chemicals used in an antimicrobial treatment process.

It should be appreciated that carrier substrate 60 may also take the form of electrospun nanofibers in the form of a mat, depending upon the thickness and durability of the electrospun nanofibers.

Figure 2:
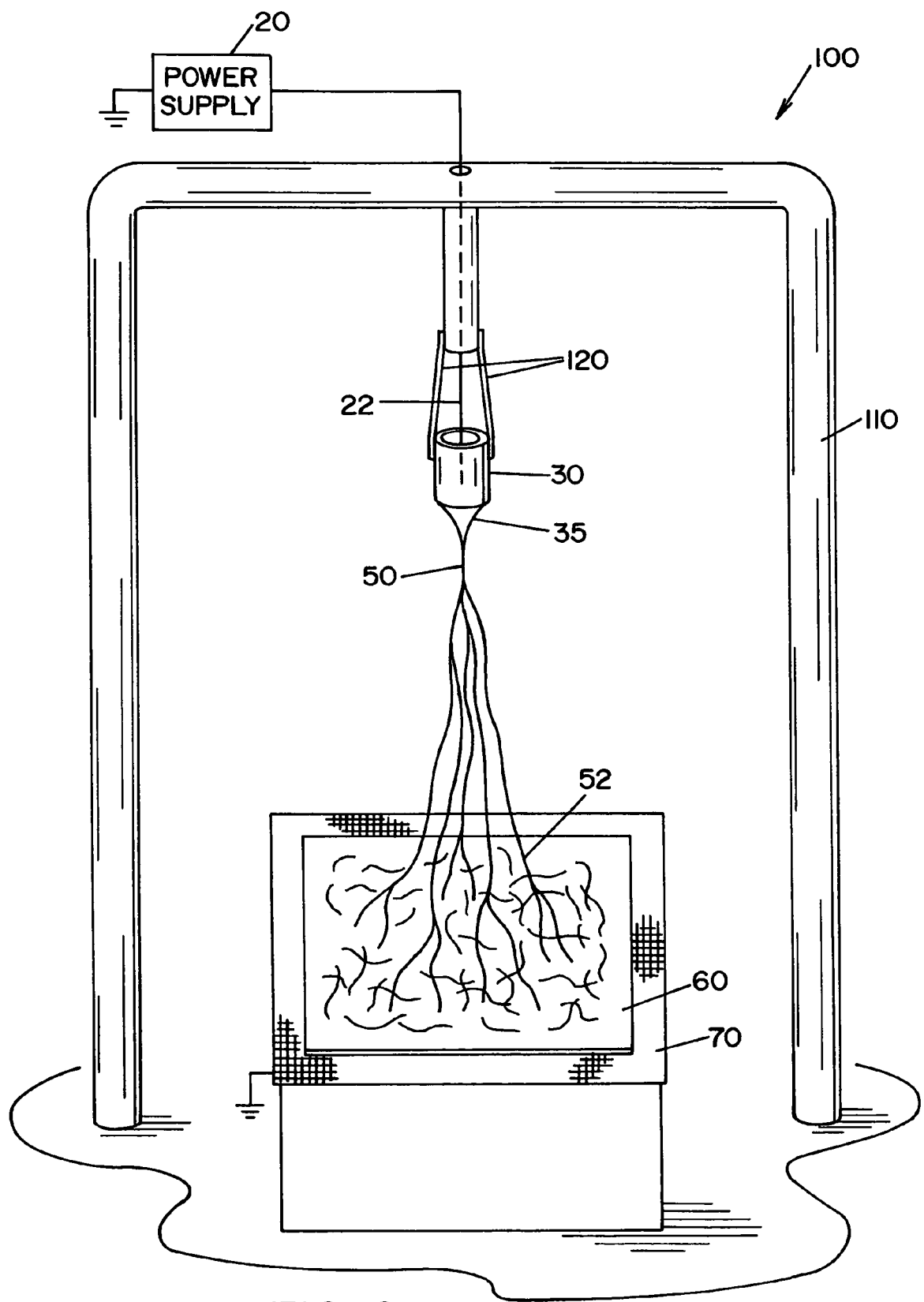
FIG. 2 illustrates an apparatus for producing electrospun nanofibers.

A physical representation of an exemplary electrospinning apparatus 100 is shown in FIG. 2. A non-conducting support structure 110 is provided to suspend capillary tube 30 above carrier substrate 60 and collector electrode 70. Capillary tube 30 is connected with support structure 110 by support members 120. Collector electrode 70 and/or carrier substrate 60 may be moveable relative to capillary tube 30. Accordingly, polymer fiber may be placed at desired locations on carrier substrate 60. It should be appreciated that multiple capillary tubes 30 may be suspended from support structure 110.

The electrospinning process can be summarized as follows. Capillary tube 30 is filled with a polymer solution 40, and electrode 22 is inserted into polymer solution 40 to charge polymer solution 40 to a high electrical potential. It should be understood that electrode 22 can also charge polymer solution 40 when it is in, connected to, or in contact with the outer wall of a metal capillary tube. Air pressure above polymer solution 40 inside capillary tube 30 may be controlled by an air pump, such that a stable drop of polymer solution 40 is suspended at the tip of capillary tube 30. It should be appreciated that polymer solution 40 may be of sufficient viscosity to sustain surface tension in capillary tube 30 without the need for an air pump. The drop of polymer solution 40 at the tip of capillary tube 30 is deformed into a conical portion 45, referred to as a Taylor cone. Electrospinning occurs when the electrical forces at the surface of polymer solution 40 overcome surface tension and cause an electrically charged liquid jet of polymer solution 40 to eject from capillary tube 30. As the jet of polymer fiber stretches and dries, radial electrical forces cause it to repeatedly splay, thereby forming a splayed portion 52. The charged polymer fiber can be directed or accelerated by the electrical forces. The polymer fibers are deposited on carrier substrate 60, as sheets or other geometric forms. The solvent added to the polymer will preferably evaporate as the jet of polymer travels from capillary tube 30 to carrier substrate 60. The polymer fibers have nanometer scale diameters (i.e., nanofibers), typically in the range of 40 to 2000 nm. Lower voltages result in thinner polymer fibers, since less force is used to pull polymer solution 40 out from capillary tube 30.

It should be appreciated that depending on the size of the active agent and solubility of the solvent, the active agent can be embedded on the outside of the nanofiber or contained within.

More details concerning the electrospinning process are found in the article by Darrell H. Reneker and Iksoo Chun entitled "Nanometre Diameter Fibres of Polymer, Produced by Electrospinning," Nanotechnology 7 (1996), pages 216-233, and the article by Jayesh Doshi and Darrell H. Reneker entitled "Electrospinning Process and Applications of Electrospun Fibers," Journal of Electrostatics 35 (1995), pages 155-160, both of which are incorporated herein by reference.

The indicator device of the present invention finds utility in a wide variety of applications, including, but not limited to, processes involving antimicrobial and antiseptic efficacy, adequate skin barrier detection, post-washing efficacy for handwashing, pre- and post-processing of food product safety, and industrial cleaning efficacy. The aforementioned processes may employ heat, liquid treatment chemicals, and/or gaseous treatment chemicals. Antimicrobial treatment processes may be carried out with use of an automated or a manual apparatus, including, but not limited to, washer/disinfectors, reprocessors and autoclaves.

By way of example and not limitation, the indicator of the present invention may be used as a biological indicator, a chemical indicator, a cleaning indicator, and a detection indicator for infection control practices. Biological indicators may be used to qualify food contact surfaces, medical device decontamination, high level disinfection, and sterilization. Chemical indicators may be used to detect use-dilution in medical reprocessing environments or residual chemistries (e.g., glutaraldehyde, peroxide). Cleaning indicators may be used after a cleaning process to detect residual chemicals on a surface, and determine adequate impingement in automated washers and clean room environments. Detection indicators for infection control practices may be used in connection with surgical site preparation, and pre- and post-operative infection control.

In accordance with a preferred embodiment of the present invention, the abovementioned electrospinning method and apparatus are used to extrude liquid polymer fibers with at least one active agent encapsulated therein to produce a nonwoven nanofiber "fabric" or mat. Preferably, each individual nanofiber has a near-uniform distribution of the active agent.

An indicator device, according to a preferred embodiment of the present invention, is generally comprised of an active agent, an encapsulation component, and a carrier substrate.

Active agents include, but are not limited to: biological agents, chemical agents, physical agents, and combinations thereof. Biological agents include, but are not limited to, spore forming bacteria (e.g., a *Bacillus* species spore), fungal spores (e.g. *Aspergillus niger*), mycobacteria, and prions (e.g. yeast PrP). Chemical agents include, but are not limited to, inorganic dyes (e.g., iron and manganese oxides, and copper sulfate) and organic dyes with photo-, thermo- and/or electrochemical-chromic properties (e.g., tetrazolium, sulfur, and lead salts), colorimetric (food colors carotenoids, oxonols, azo- and aza-compounds, nitro and nitroso-compounds, carbonyl, and quinone/anthraquinone compounds), fluorescence (e.g. rhodopsin), phosphorescence, and chemiluminescence (e.g. luciferin), biological dyes (crystal violet), redox dyes, and crown ethers to detect metal ions. A complete list and description of dyes and pigments can be found in the book by Henrich Zollinger entitled, "Color Chemistry: Syntheses, Properties and Applications of Organic Dyes and Pigments," VCH Verlagsgesellschaft mbH: Weinheim, Germany, 1987.

It should be appreciated that in an alternative embodiment of the present invention, the chemical agents may function to neutralize (e.g., catalase) an antimicrobial chemistry after a treatment process. In this case, the indicator device is located remote from the treatment environment and accessed by the antimicrobial chemistry for the purpose of neutralizing it after the treatment process.

Antimicrobial chemistries include, but are not limited to, chlorine and chlorine compounds (e.g., hypochlorite, triclosan, PCMX, chlorinated biguanides such as chlorhexidine), peroxygens (e.g., hydrogen peroxide, mono- or dipercarboxylic acids, monopersulfate), alcohols (e.g. isopropyl-, ethyl-), phenolic compounds, iodine compounds (e.g., PVP-I), cationic surfactants (Quaternary Ammonium Compounds), anionic and nonionic surfactants, and food and industrial grade preservatives (e.g., benzoic acid derivatives, sorbic acids, and natural and essential oils with pesticidal efficacy), and any combination thereof. Antimicrobial chemistries may also include antimicrobials with increased activity when in the form of a nanoemulsion (e.g., Nanostat from NanoBio Corp, and Ecotrue from Envirosystems). Such nanoemulsions are made by imparting oil/water emulsions of oils, surfactants, and chloro-xylenols (PCMX). A complete list of antimicrobial compounds can be found in the book by Seymour Block entitled, "Disinfection, Sterilization, and Preservation," $3^{rd}$ through $5^{th}$ edition, herein fully incorporated by reference.

Physical agents include, but are not limited to, polymers, non-polymers, supports systems, and markers that provide detection of treatment process parameters, microelectrode materials or electrochemical sensor materials, or both, nano-carbon tube, and RFID tags.

Physical agents provide a means to insure adequate indication of various degrees of effectiveness of an antimicrobial treatment process and/or various degrees of effectiveness of a phase of an antimicrobial treatment process having multiple phases.

In accordance with an alternative embodiment of the present invention, physical agents within the nanofibers can be used to neutralize an antimicrobial treatment chemistry after the process, especially physical agents that generate a plasma gas field or electric field, or agents that stabilize free radicals (e.g. hydroxyl groups, hydrogen peroxide, ozone). In this case, the indicator device is located remote from the treatment environment and accessed by the antimicrobial chemistry for the purpose of neutralizing it after the treatment process.

It should be appreciated that polymer deposition can be arranged to accommodate, protect, or encapsulating miniature metals and other solid state materials that function as a trip, signal relay or signal transponder system to measure, indicate, or record critical parameters when interrogated or in real time. Also, polymer fibers containing MEMS (Micro-Electro-Mechanical Systems) components can be made as microarrays used to screen a sample for microorganisms.

As indicated above, different types of active agents may be used in combination. For example, an indicator device may include both a physical agent and a chemical agent. The physical agent breaks down during an antimicrobial treatment process to expose a chemical agent to the process environment. In this regard, the physical agent has pressure, heat, or time-sustaining properties that prevent the chemical agent from being exposed to treatment chemicals until a predetermined period of time has elapsed, or until a predetermined stage of the antimicrobial treatment process has commenced.

The encapsulation component encapsulates at least one active agent to reduce "wash-off," and may control the reaction between the active agent and treatment chemicals. Preferably, the encapsulation component is comprised of a material that is biologically and chemically inert, has a controlled adhesion strength to the carrier substrate, and is permeable to the treatment chemicals of the antimicrobial treatment process. In accordance with a preferred embodiment of the present invention, the encapsulation component is selected from the group including, but not limited to, a polymer; a polymer blend; and a mixture of a polymer and a plasticizer. The polymer may include any solid or liquid high-molecular weight polymer obtained by conducting a polymerization reaction, or produced by "drying components" capable of creating a polymer, pseudopolymer, and the like. Drying components may include solvents that remove water (e.g. acetone), agents that absorb/adsorb a solvent (e.g., polyacrylates, chitosan), polymerizers/placticizers (e.g., oxidizers), or heat or electrical energy produced through the apparatus electrodes (e.g., plasma gas) or by activation of the physical agents (e.g., electroactive polymers, superconducting metals, and MEMS) in the electrospun polymer.

By way of example, and not limitation, the polymer or polymer blend may include one or more of the following: polycaprolactone (a biodegradable polymer); pluronic acid; Tecophilic® family of highly water absorbing, aliphatic, polyether-based thermoplastic polyurethanes, from Thermedics Polymer Products, that have been specially formulated to absorb equilibrium water contents of up to 150% of the weight of dry resin; Tecoflex® family of highly water phobic, aliphatic, polyether-based thermoplastic polyurethanes from Thermedics Polymer Products; polymeric gels that are insoluble in water, including, but not limited to, co-polymers of polyvinylpyrolidone, polyacrylamide, polyvinyl alcohol, cross-linked polyacrylates, polyethyleneimine, and the like; polymer resins, including, but not limited to, Carbopol® from B.F. Goodrich; cellulose-based polymers, including, but not limited to, ethylcellulose; biologically derived polymers, including, but not limited to collagen, polyhydroxy-aldehydes and ketones (e.g. glucose, galactose); peptides (serum albumin); and shellac. Polymers with active binding sites for halogens (e.g. chlorine) such as polystyrene hydantoin (Halopure®) from Vanson-Halosource, quaternary amines (Microban Shield®) from Aegis, and acrylates and olefins are also suitable.

The encapsulation component may also include a solvent for liquefying the polymer or polymer blend. By way of example, and not limitation, the solvent may be selected from the following: water ($H_2O$), tetrahydrafuran (THF), ethanol (EtOH), acetone, isopropanol, and combinations thereof. Ionic liquids such as N-methylimidazole from BASF Corporation may be used as alternatives to the aforementioned organic solvents. The ionic liquids themselves may be capable of polymerizing and forming a polymer mat, and as such eliminate the need for the aforementioned solvents.

It should be understood that the selected solvent should not inactivate the active agent encapsulated within the polymer. For instance, suitable combinations of polymers and solvents for encapsulation of spores, include, but are not limited to: (1) polycaprolactone and acetone; (2) pluronic acid and ethanol; and (3) Tecoflex® and tetrahydrafuran (THF), (4) albumin and water, and (5) N-halamine polymers and dimethylsulfoxide, as described in detail in U.S. Pat. No. 6,294,185, issued to Worley et al., Sep. 25, 2001, entitled "Monomeric and Polymeric Cyclic Amine and N-Halamine Compounds."

The active agent may be directly incorporated into an encapsulation component, or the active agent may be deposited onto a carrier substrate and be sealed thereon by an encapsulation component. For instance, high level disinfection and decontamination of surfaces may be validated/indicated by means of an active agent, such as a heat sensitive marker or a dry-resistant organism (non-pathogenic).

As indicated above, the carrier substrate is preferably a rigid porous or nonporous material. By way of example, and not limitation, the carrier substrate may be formed of a plastic sheet or film, a teflon coating, woven or non-woven fibers (e.g., cotton, cloth, and plant derived cellulose), paper, aluminum foil, and stainless steel. Furthermore, the carrier substrate may be formed from the polymer solution as an end result of electrospinning the liquefied polymer. Also, the deposition of the charged polymer onto the carrier substrate at the ground plate or mesh during the electrospinning process can be coupled with thermal or nonthermal plasma grafting processes to enhance the uniformity and binding strength of the polymer onto the carrier substrate.

A biological indicator according to the present invention may include spores that are encapsulated into an electrospun nanofiber, as described above. For example, a genetically modified *Bacillus* species (e.g., *stearothermophilis* in heat-based systems) with a chromosomally-integrated indicator, foreign gene (e.g., the gene for firefly luciferase) may be encapsulated into the nanofiber. The foreign gene is integrated into chromosomal operons that are not expressed during the sporulation cascade, but are expressed early in a germination cascade. The foreign gene product is not present in the spore, but on germination would be expressed, and thus detected by a variety of available rapid-detection systems.

As noted above, cleaning indicators can be used to detect residuals on a surface following a cleaning process. An active agent is encapsulated within an encapsulation component, and sustained indefinitely until such time that the active agent is affected by the cleaning process. In accordance with a preferred embodiment, the active agent is a chemical resistant to biological, chemical, and physical degradation; soluble in the encapsulation component (e.g., a polymer compound); and provides a calorimetric change when exposed to the treatment chemicals of the cleaning process. By way of example, and not limitation, the active agent for a cleaning indicator may be selected from the group including, but not limited to, a water-soluble dye (e.g., a pH indicator dye such as phenol red, methylene blue and Azo compounds), and a fluorescent marker.

The present invention also finds advantageous application as an antimicrobial fabric for simulating a surgical barrier site, as will be described by example below, and as an antimicrobial delivery agent.

With regard to an antimicrobial delivery agent, an antimicrobial agent may be encapsulated as an active agent into the encapsulation component for application to surfaces, to permit slow release over time. For example, biocides (including, but not limited to, chlorhexidine and triclosan in formulation) may be encapsulated and directly applied to a skin surface. This allows for a "slow-release" of the antimicrobial agent for bioburden reduction/control, such as bioburden reduction for preoperative preparation or bioburden control at wound sites or points of surgical entry (e.g., catheter entry sites).

In accordance with an alternative embodiment of the present invention, the indicator device may have multiple layers of encapsulation components. For instance, a first layer encapsulation component covers a second layer encapsulation component, where the second layer encapsulation component encapsulates an active agent. The multiple layers of encapsulation components may be selected to provide an indicator device that indicates the efficacy/adequacy of an enzymatic, pH or other cleaning chemistry process. For example, a first layer encapsulation component may be comprised of a first polymer, while the second layer encapsulation component may be comprised of an insoluble polymer that encapsulates a dye mix. The first layer encapsulation component is removed during a cleaning process, thereby exposing the second layer encapsulation component. The active agent encapsulated in the second layer encapsulation component changes color to provide an indication of the efficacy of the cleaning process.

It should be appreciated that the encapsulation component (e.g., polymer) itself may be used to determine the effectiveness of an antimicrobial treatment process. In this regard, when multiple layers of encapsulation components are applied to a carrier substrate, each layer may have different adhesion strengths to the carrier substrate or subsequent layers of encapsulation components, or the concentrations of the polymer or polymer blend are adjusted in series to provide a scale for process effectiveness. For example, a polymer solution including hydrophilic and hydrophobic polymers can be adjusted such that the hydrophobic polymer concentration is greater than the hydrophilic polymer concentration to minimize wash-off in high flow liquid processes. The balance of the solution contains a hydrophilic polymer in a concentration suitable to permit penetration of the treatment active. A preferred concentration is 70% hydrophobic polymer (e.g., tecoflex) and 30% hydrophilic polymer (e.g., pluronic acid).

The present invention will now be further described by way of the following examples:

EXAMPLE 1

Biological Indicator

| | |
|---|---|
| Encapsulation Component | Polyurethane 67% Tecoflex and a water soluble polymer (33% Pluronic acid) Solvent: Tetrahydrofuran (THF) |
| Active Agent | Spore *Bacillus stearothermophilus* ATCC 12980 |
| Carrier Substrate | Polymer Mat |

In Example 1, a nanofiber biological indicator (BI) was produced using the electrospinning process described above to compare the level of wash-off against commercially available paper impregnated BI's. These BI's typically lose approximately 50% of the indicator organism solely due to mechanical action of water in automated liquid systems. In this regard, spores were incorporated into a polymer blend of polyurethane and a water soluble polymer. The nanofiber BI was sectioned and cut into two 3 cm$^2$ samples containing approximately $2.35 \times 10^7$ (7.37 $\log_{10}$) colony forming units (CFU) *Bacillus stearothermophilus* ATCC 12980 per sample. To simulate the process conditions that can cause wash-off in liquid-based automated reprocessing systems, the impact of agitation to remove the indicator organism was evaluated in vitro by vigorously vortexing the samples in 10 milliliters (mL) deionized water (DI) 5 times; each time vortexing for 3 seconds. Several observations were made as to the effectiveness of the polymer to retain the test organisms and to show reproducibility in results. Overall, the total wash-off after all 5 washings were 2.5 and $2.9 \times 10^3$ CFU (0.01%) for each sample. The wash-off between each washing was very low, ranging from 1.6 to $9.3 \times 10^2$ CFU. Furthermore, the wash-off from each subsequent wash compared to the initial wash was exhaustive as less wash-off occurred after each subsequent washing. The initial wash-off values for the samples between 7.5 and $9.3 \times 10^2$ CFU, and were reduced to 1.2 to $1.6 \times 10^2$ CFU after the fifth wash. As a result, the polymer BI outperformed commercial BI's by retaining 99.99% of the test organism as compared to approximately 50%. In a separate test, the ability of an active agent to penetrate the nanofiber BI and inactivate the test organism was investigated. Samples as prepared above were treated in vitro with a 0.2% peracetic acid/builders solution (i.e., STERIS 20 Sterilant Concentrate) at 50° C. over 10, 40, 80, and 120 seconds, removed, and neutralized in 0.048% sodium thiosulfate. The samples were then dissolved in a low concentration of non inhibitory THF solvent to dissolve the polymer and quantify the remaining test organism. Serial dilutions were performed in Tryptic soy broth and aliquots of the appropriate dilutions dispensed onto pour plates of Tryptic Soy Agar. Based on the results, the active agent was permitted to pentrate the polymer to contact and kill the test organism as shown by an initial reduction at 10 seconds of 0.78 $\log_{10}$ and a significant reduction at 120 seconds of 5.8 $\log_{10}$. Based on the kill rate shown above, it can be assumed that at longer exposure times beyond 120 seconds, all of the test organism in the BI would have been inactivated.

A nanofiber BI has several advantageous characteristics over conventional biological indicators. In this respect, the nanofiber BI is durable; the nanofiber BI can be penetrated by a liquid antimicrobial treatment chemical; the nanofiber BI does not affect the qualitative medium used to detect the presence of a test organism; the nanofiber BI has a wall strength that allows a spore to outgrow; wash-off of spores is minimized by formation of nanofiber around the spores; accuracy of wash-off qualification is improved by uniform distribution of spores throughout the nanofiber BI; the electrospinning process provides a sterile environment without the need for a clean room; a nanofiber BI is ready for use after being manufactured without a drying period; a nanofiber BI may not require special packaging and does not add restrictions to the shelf life of the BI because the spores are encapsulated within the nanofiber.

EXAMPLE 2

Chemical Indicator

| | |
|---|---|
| Encapsulation Component | Polyurethane Tecoflex<br>Solvent: Tetrahydrofuran (THF) |
| Active Agent | Color changing chemical: 0.16% crystal violet |
| Carrier Substrate | Polymer Mat |

The chemical indicator (CI) includes a color changing chemical (i.e., crystal violet) that is sensitive to oxidizing chemistry, such that upon oxidation with an antimicrobial treatment chemical (i.e., STERIS 20 sterilant), comprised of 0.2% peracetic acid (PAA) in a builder package containing buffers, anticorrosives, and chelating agents will cause a color change. The baseline color of the CI is deep purple, and changes to a white color in the presence of >1500 mg/L of the sterilant STERIS 20.

It should be appreciated that other dyes/pigments can be encapsulated in the encapsulation component to verify other parameters of the antimicrobial treatment process, including, but not limited to, time and temperature.

EXAMPLE 3

Cleaning Indicator

| | |
|---|---|
| Encapsulation Component | Polyurethane 67% Tecoflex and<br>a water soluble polymer (33% pluronic acid)<br>Solvent: Tetrahydrofuran (THF) |
| Active Agent | Color changing chemical: 7% blue ink |
| Carrier Substrate | Stainless steel coupon |

The cleaning indicator (CnI) of Example 3 is used to test the efficacy of a cleaning agent of an automated cleaning system that penetrates and removes soil, debris and contaminants using a high pressure spray. In Example 3, the CnI converted from a baseline yellow color to a deep blue color upon contact with water for 30 seconds.

EXAMPLE 4

Antimicrobial Surgical Site Barrier

| | |
|---|---|
| Encapsulation Component | Polyurethane (67% Tecoflex) and<br>a water soluble polymer (33% Pluronic acid) |
| Active Agent | Chlorhexidine Gluconate (CHG) in ethanol<br>Concentration Range: 0.5% to 1% |

The effectiveness of the CHG polymer mat was investigated using a disk diffusion method on *Staphylococcus aureus* ATCC 6538 and *Escherichia coli* ATCC 25922 lawn plates. The plates were prepared for each organism by dispensing and spreading 0.1 mL of the bacterium over the entire surface of prepared tryptic soy agar plates to create a "lawn." Concentrations of chlorhexidine gluconate (CHG) at 0.25%, 0.5%, and 1.0% were electrospun with Tecoflex to produce an antimicrobial polymer mat. The polymer mats were cut into two 0.5-1.0 inch diameter disks for each CHG concentration. One disk per plate was placed into the center of the bacterial plate The plates were then incubated at 37° C. for 7 days to determine the zone of inhibition or antimicrobial coverage around the disk (measured in millimeters diameter), which simulates the persistence of an antimicrobial dressing to inactivate resident microorganisms on the skin. For *S. aureus,* 0.25%, 0.50%, and 1.0% CHG was effective showing mean zones of 20 mm, 25 mm, and 25 mm zones, respectively at 7 days, while at the same concentrations *E. coli* mean zones were 11 mm, 23 mm, and 28 mm. By these results it is apparent that the CHG polymer is capable of inactivating resident microorganisms and shows minimal leaching and sustained release of the CHG by maintaining the zones over 7 days.

The nanofiber of Example 4 provides a barrier that maintains an air exchange to the environment without allowing external organisms to invade. Furthermore, the delivery of the active agent is localized and sustained over an extended period of time. Accordingly, a greater amount of the active agent is in contact with the microorganisms, and prevents their proliferation. The nanofiber can remain in contact with the skin during an operation, or at a device (e.g., catheter) insert site to provide controlled release of the active agent around an incision or orifice. In a preferred embodiment, the nanofiber is biodegradable.

It has been recognized that surgical site infections are a leading cause of post-surgical infections. Antimicrobial chemicals (e.g., chlorhexidine (CHG) or polyvinylpyrrilodone iodine (PVP-I)) are used to reduce the risks of infection. However, it has been observed that little of the antimicrobial chemical is effective against microbes, because penetration is superficial and may not reach areas where microorganisms (e.g., bacteria) reside on the skin.

Other modifications and alterations will occur to others upon their reading and understanding of the specification. For example, the nanofibers of the present invention may be arranged into a bar code configuration, or other machine readable code format. It is intended that all such modifications and alterations be included insofar as they come within the scope of the invention as claimed or the equivalents thereof.

Having described the invention, the following is claimed:

1. An indicator device for use in determining the efficacy of an antimicrobial treatment process that includes a first process, comprising:
   an active agent responsive to exposure to a chemical of the antimicrobial treatment process;
   a carrier substrate;
   a first encapsulation component comprised of electrospun nanofibers including a first polymer, wherein the active agent is encapsulated by the first encapsulation component, the electrospun nanofibers of the first encapsulation component are deposited onto the carrier substrate in an electrospinning process; and
   a second encapsulation component comprised of electrospun nanofibers including a second polymer, wherein the electrospun nanofibers of the second encapsulation component are deposited onto the first encapsulation component in an electrospinning process, thereby covering the first encapsulation component, said second encapsulation component removable during the first process of the antimicrobial treatment process to expose the first encapsulation component to the chemical of the antimicrobial treatment process.

2. An indicator device according to claim 1, wherein said active agent is embedded on the outside of the electrospun nanofibers of the first encapsulation component.

3. An indicator device according to claim 1, wherein said active agent is embedded within the electrospun nanofibers of the first encapsulation component.

4. An indicator device according to claim 1, wherein said first polymer is an insoluble polymer.

5. An indicator device according to claim 4, wherein said active agent is a dye mix.

6. An indicator device according to claim 4, wherein said first process is a cleaning process.

7. An indicator device according to claim 1, wherein said active agent is a biological agent, a chemical agent, a physical agent, or combinations thereof.

8. An indicator device according to claim 7, wherein said chemical agent is an inorganic dye with photo-, thermo- and/or electrochemical-chromic properties, an organic dye with photo-, thermo- and/or electrochemical-chromic properties, colorimetric, fluorescence, phosphorescence, or chemiluminescence properties, biological dyes, redox dyes, crown ethers to detect metal ions, or combinations thereof.

9. An indicator device according to claim 8, wherein said colorimetric property is food colors carotenoids, oxonols, azo-compounds, aza-compounds, nitro-compounds, nitroso-compounds, carbonyl, quinone-compounds or anthraquinone-compounds.

10. An indicator device according to claim 7, wherein said chemical agent is an iron oxide, a manganese oxide, copper sulfate, tetrazolium, sulfur, or lead salt.

11. An indicator device according to claim 7, wherein said active agent provides a colorimetric change in response to exposure to said chemical of the antimicrobial treatment process.

12. An indicator device according to claim 11, wherein said active agent is a water-soluble dye or a fluorescent marker.

13. An indicator device according to claim 12, wherein said water-soluble dye is a pH indicator dye.

14. An indicator device according to claim 13, wherein said pH indicator dye is phenol red, methylene blue or Azo compounds.

15. An indicator device according to claim 7, wherein said physical agent is selected from the group consisting of: polymers, non-polymers, supports systems, markers that provide detection of treatment process parameters, microelectrode materials, electrochemical sensor materials, nanocarbon tube, RFID tags, and combinations thereof.

16. An indicator device according to claim 1, wherein said biological agent is selected from the group consisting of a spore forming bacteria, a fungal spore, mycobacteria, and prions.

17. An indicator device according to claim 1, wherein adhesion strength of the first encapsulation component is different from adhesion strength of the second encapsulation component.

18. An indicator device according to claim 1, wherein said encapsulation component includes at least one of the following: (a) a polymeric gel that is insoluble in water, (b) a polymer resin, (c) a cellulose-based polymer, (d) a biologically derived polymer, (e) peptides, (f) shellac, (g) a polymer with active binding sites for at least one of halogens, quaternary amines, acrylates, olefins, or combinations thereof 19. An indicator device according to claim 18, wherein said encapsulation component encapsulates at least one of the following: a miniature metal, a solid state material, or MEMS (Micro-Electro-Mechanical Systems).

20. An indicator device according to claim 18, wherein said polymeric gel is co-polymers of polyvinylpyrolidone, polyacrylamide, polyvinyl alcohol, cross-linked polyacrylates, or polyethyleneimine.

21. An indicator device according to claim 18, wherein said cellulose-based polymer is ethylcellulose.

22. An indicator device according to claim 18, wherein said biologically derived polymer is collagen, polyhydroxy-aldehydes or ketones.

23. An indicator device according to claim 1, wherein said encapsulation component includes at least one of the following: polycaprolactone; pluronic acid; a polyether-based thermoplastic polyurethane; a polymeric gel that is insoluble in water; a polymer resin, and a cellulose-based polymer, albumin, and N-halamine polymers.

24. An indicator device according to claim 1, wherein said encapsulation component includes a solvent.

25. An indicator device according to claim 24, wherein said solvent is tetrahydraftran (THF), ethanol (EtOH), acetone, isopropanol, water, an ionic liquid, dimethylsulfoxide, or combinations thereof.

26. An indicator device according to claim 1, wherein said carrier substrate is a rigid porous or nonporous material.

27. An indicator device according to claim 26, wherein said carrier substrate is stainless steel, woven fibers, non-woven fibers, glass, or plastics.

* * * * *